(12) United States Patent
Schubert

(10) Patent No.: US 7,676,328 B2
(45) Date of Patent: Mar. 9, 2010

(54) METHOD FOR IDENTIFYING CELL-SPECIFIC PROTEINS

(75) Inventor: Walter Schubert, Biederitz (DE)

(73) Assignee: MPB Meltec Patent-und Beteiligungsgesellschaft MbH, Magdeburg (DE)

( * ) Notice: Subject to any disclaimer, the term of this patent is extended or adjusted under 35 U.S.C. 154(b) by 0 days.

(21) Appl. No.: 10/129,316

(22) PCT Filed: Aug. 31, 2001

(86) PCT No.: PCT/EP01/10075

§ 371 (c)(1),
(2), (4) Date: Jul. 16, 2002

(87) PCT Pub. No.: WO02/21137

PCT Pub. Date: Mar. 14, 2002

(65) Prior Publication Data

US 2003/0096318 A1    May 22, 2003

(30) Foreign Application Priority Data

Sep. 4, 2000 (DE) .................. 100 43 470

(51) Int. Cl.
*G01N 33/48* (2006.01)
(52) U.S. Cl. ............................................. 702/19
(58) Field of Classification Search ............... 702/19, 702/20; 703/11; 435/6, 91.2; 536/23.1; 530/350; 436/86, 536, 517, 501, 512, 518
See application file for complete search history.

(56) References Cited

U.S. PATENT DOCUMENTS

| 5,965,366 A | 10/1999 | Ochoa et al. | |
| 6,165,464 A * | 12/2000 | Hudziak et al. | 424/142.1 |
| 6,670,194 B1 * | 12/2003 | Aebersold et al. | 436/173 |

FOREIGN PATENT DOCUMENTS

| DE | 197 09 348 C2 | 12/1997 |
| DE | 100 14 685 A1 | 10/2001 |
| DE | 100 14 708 A1 | 10/2001 |
| EP | 0 810 428 A2 | 12/1997 |
| WO | WO 98/19271 | 5/1998 |
| WO | WO 99/55381 | 11/1999 |
| WO | WO 00/29848 A3 | 5/2000 |
| WO | WO 00/49410 A3 | 8/2000 |

OTHER PUBLICATIONS

Emmert-Buck, M.R., et al: "Approach to Proteomic Analysis of Human Tumors," Molecular Carcinogenesis 27 : 158-165 (2000), publ. Wiley-Liss, Inc., New York, NY, US.
Lopez, Mary F.: "Proteome analysis—I. Gene products are where the biological action is," Journal of Chromatography B. 722 (1999) 191-202; Elsevier Science Publishers, NL.
Pandey, A., et al: "Proteomics to study genes and genomes," Nature, (Jun. 15, 2000) 405 (6788) 837-46. Ref: 88. (Abstract from Medline, PubMed ID: 10866210).
Witzmann, F.A., et al.: "Differential expression of cytosolic proteins in the rat kidney cortex and medulla : preliminary proteomics," Electrophoresis, (Oct. 1998) 19 (14) 2491-7. (Abstract from Medline, PubMed ID: 9820973).

* cited by examiner

*Primary Examiner*—Jerry Lin
(74) *Attorney, Agent, or Firm*—Weingarten, Schurgin, Gagnebin & Lebovici LLP

(57) ABSTRACT

The present invention relates to a method for identifying cell-specific proteins comprising the following steps: a) determining cell-specific protein combination patterns of n cells; b) comparing the protein combination patterns of healthy and pathologically or physiologically modified cells of one cell type or comparing the protein combination patterns of cells of a different cell type affected by the same disease; c1) subtracting the coincident parts of the protein combination patterns of healthy and pathologically or physiologically modified cells of one cell type compared in step b) and determining a cell-specific protein resulting therefrom; or c2) subtracting the non-coincident parts of the protein combination patterns of cells of a different cell type affected by the same disease compared in step b) and determining a cell-specific protein resulting therefrom; and d) identifying the resulting cell-specific protein in terms of molecules and spatial structure.

16 Claims, No Drawings

METHOD FOR IDENTIFYING CELL-SPECIFIC PROTEINS

DESCRIPTION

The present invention relates to a method for identifying cell-specific proteins.

The identification of cell-specific protein combination patterns is a crucial factor for elucidating cell-to-cell interactions which may cause countless effects within an organism. Especially the knowledge of disease-specific target structures is a decisive prerequisite for the development of effective medications which at the same time have only few side-effects.

It is known that immune cells (lymphocytes) will express specific protein combinations—also referred to as protein combination patterns or (abbreviated) PCP—which are responsible for a binding to endothelial cells of the blood vessels in the brain and in muscle tissue. Other protein combinations, by contrast, will not cause such binding to these endothelial cells. Surprisingly, these specific combinations are inter-individually constant, always exhibiting the same binding functions. The specific protein combination patterns therefore seem to be an inter-individually constant lymphocyte binding code of the cell surface for organ-specific endothelial cell surfaces which constitutes a cell-specific target structure. Cell-specific target structures may thus include very specific protein combination patterns.

Invasive tumor cells also exhibit specific protein combination patterns on their cell surfaces which result in a specific, i.e. organ-selective, invasive behavior. Such protein combination patterns therefore constitute target structures for potential medications.

However, an absolute prerequisite for the development of such highly selective medications is the knowledge of the molecular composition of these target structures.

Methods for identifying target structures are known in the prior art, which are based on the analysis of gene expression profiles of diseased tissues or cells as compared to gene expression profiles of healthy tissues or cells, with protein expression profiles as well as expression profiles of the messenger ribonucleic acid (mRNA) being intended to provide information on the appearance of new proteins, malregulated or abnormally modified proteins in diseased tissues or cells (e.g. in: F. Lottspeich/H. Zorbas; Bioanalytik; Spektrum Akademischer Verlag; Heidelberg, 1998).

However, these methods all use cell homogenates usually produced from thousands or millions of cells since only such vast amounts of cells will allow expression profiles of the abovementioned kind to be established. The cells contained in the cell homogenates have been solubilized so as to allow the extraction and separation of the proteins or mRNA molecules by means of biochemical processes.

A shortcoming of these prior art methods, however, is that they are not suitable for identifying protein combination patterns, since the individual protein components of such a protein combination pattern will be completely separated by the generation of cell homogenates and by the subsequent extraction processes, and the fundamental information relating to their cell- and tissue-topological location will be lost. Furthermore, owing to the destruction of the cell compartments, no information can be gained any longer regarding the combinations of proteins within these cell compartments and their relative topological relation to each other.

Moreover, another disadvantage of the prior art processes is that no analyses can be performed at an individual level, making it impossible to detect differences of the individual cells with respect to their protein combination patterns. These disadvantages are overcome by the methods disclosed in DE 197 09 348 C2 and DE 100 14 685 A1 for determining, identifying and mapping cell-specific target structures. These methods can be used for comparatively examining protein combination patterns of individual cells or cell membranes of different cell or tissue samples. In doing so, those marker molecules can be identified which will bind to e.g. a certain protein combination pattern or to a certain area of such a protein combination pattern of a first object stemming from a first tissue or cell sample, and which will at the same time not bind to a second object stemming from a second tissue or cell sample. By means of these identified marker molecules, using a sample portion of the first tissue and/or cell sample, those molecular areas (molecules or molecular complexes) of the protein combination pattern may now be located and/or selected and subsequently characterized which are bound by the identified marker molecules. This will allow the detection and understanding of the molecular composition of a protein combination pattern, of the arrangement of the molecules within said protein combination pattern as well as of the arrangement of the protein combination pattern within a tissue or a cell.

The cell-specific protein combination patterns thus obtained, however, will still be highly complex—which will clearly aggravate the development of highly selective medications.

It is therefore the object of the present invention to further improve on and provide a method of the above-mentioned type which will further process identified and highly complex protein combination patterns, thus facilitating the development of highly selective medications.

This object is accomplished by a method of the invention for identifying cell-specific proteins comprising the following steps: (a) determining cell-specific protein combination patterns of n cells; (b) comparing the protein combination patterns of healthy and pathologically or physiologically modified cells of one cell type or comparing the protein combination patterns of cells of a different cell type affected by the same disease; (c1) subtracting the coincident parts of the protein combination patterns of healthy and pathologically or physiologically modified cells of one cell type compared in step (b) and determining a cell-specific protein resulting therefrom; or (c2) subtracting the non-coincident parts of the protein combination patterns of cells of a different cell type affected by the same disease compared in step (b) and determining a cell-specific protein resulting therefrom; and (d) identifying the resulting cell-specific protein in terms of molecules and spatial structure.

Reducing the highly complex protein combination patterns thus determined to a single, highly selective and cell-specific protein will clearly facilitate the development of likewise highly selective medications, at the same time significantly shortening the time required for such development. Thus it will no longer be required in the development of medications to investigate the highly complex and likewise cell-characteristic protein combination patterns.

The invention merely requires a selection of a substance for suppressing the activity of the identified cell-specific protein. Such suppression will cause the cell-specific protein network, and hence the cell functions, to collapse. For example, switching off the cell-specific protein of tumor cells will in turn suppress the migration of these cells since the protein identified in this process controls and regulates the migration behavior of the tumor cell. The suppressing substance in this case may be an antibody.

Particular advantages of the method according to the invention will be obtained if pathologically modified cells are of the invasive type.

The knowledge of these e.g. disease-specific proteins within a protein combination pattern will moreover allow the development of highly specific medications which will be almost without undesired side effects owing to this very specificity.

The cell-specific protein combination patterns to be processed according to the invention will be determined by means of the methods disclosed in DE 197 09 348 C2 and DE 100 01 685 A1 for determining, identifying and mapping cell-specific target structures.

The invention claimed is:

1. A method for identifying proteins specific to a modified cell type, the method comprising the following steps:
    a) determining experimentally topological protein combination patterns of a plurality of individual cells or cell membranes from a sample of healthy cells;
    b) determining experimentally topological protein combination patterns of a plurality of individual cells or cell membranes from a sample of pathologically or physiologically modified cells of the same cell type as the healthy cells of a);
    c) subtracting the coincident parts of the topological protein combination patterns determined in a) and b) from the protein combination patterns determined in b), leaving a residual topological protein combination pattern comprising one or more proteins, wherein said one or more proteins of the residual topological protein combination pattern of step c) are identified as proteins specific to said modified cell type; and
    d) outputting said identified proteins.

2. The method of claim 1, further comprising the step of selecting a substance for suppressing the activity of one or more identified cell-specific proteins.

3. The method of claim 2, wherein the substance is an antibody.

4. The method of claim 1, wherein the pathologically modified cells are of an invasive type.

5. The method of claim 2, wherein the pathologically modified cells are of an invasive type.

6. The method of claim 3, wherein the pathologically modified cells are of an invasive type.

7. A method for identifying disease-specific proteins, the method comprising the following steps:
    a) determining experimentally topological protein combination patterns of a plurality of individual cells or cell membranes from a sample of cells of a first cell type, the cells affected by a disease;
    b) determining experimentally topological protein combination patterns of a plurality of individual cells or cell membranes from a sample of cells of a second cell type, the cells affected by said disease;
    c) subtracting the non-coincident parts of the topological protein combination patterns determined in a) and b) from either the protein combination patterns determined in a) or from the protein combination patterns determined in b), leaving a residual topological protein combination pattern comprising one or more proteins, wherein said one or more proteins of the residual topological protein combination pattern of step c) are identified as disease-specific proteins of said disease; and
    d) outputting said identified proteins.

8. The method of claim 7, further comprising the step of selecting a substance for suppressing the activity of the one or more identified disease-specific proteins.

9. The method of claim 8, wherein the substance is an antibody.

10. The method of claim 7, wherein the disease-affected cells are of an invasive type.

11. The method of claim 8, wherein the disease-affected cells are of an invasive type.

12. The method of claim 9, wherein the disease-affected cells are of an invasive type.

13. A method for identifying proteins specific to a modified cell type, the method comprising the following steps:
    a) determining at a microscopic level topological protein combination patterns of a plurality of individual cells or cell membranes from a sample of healthy cells;
    b) determining at a microscopic level topological protein combination patterns of a plurality of individual cells or cell membranes from a sample of pathologically or physiologically modified cells of the same cell type as the healthy cells of a);
    c) subtracting the coincident parts of the topological protein combination patterns determined in a) and b) from the protein combination patterns determined in b), leaving a residual topological protein combination pattern comprising one or more proteins, wherein said one or more proteins of the residual topological protein combination pattern of step c) are identified as proteins specific to said modified cell type; and
    d) outputting said identified proteins.

14. A method for identifying disease-specific proteins, the method comprising the following steps:
    a) determining at a microscopic level topological protein combination patterns of a plurality of individual cells or cell membranes from a sample of cells of a first cell type, the cells affected by a disease;
    b) determining at a microscopic level topological protein combination patterns of a plurality of individual cells or cell membranes from a sample of cells of a second cell type, the cells affected by said disease;
    c) subtracting the non-coincident parts of the topological protein combination patterns determined in a) and b) from either the protein combination patterns determined in a) or from the protein combination patterns determined in b), leaving a residual topological protein combination pattern comprising one or more proteins, wherein said one or more proteins of the residual topological protein combination pattern of step c) are identified as disease-specific proteins of said disease; and
    d) outputting said identified proteins.

15. A method for identifying proteins specific to a modified cell type, the method comprising the following steps:
    a) providing a first cell sample comprising healthy cells and a second cell sample comprising pathologically or physiologically modified cells of the same cell type as said healthy cells;
    b) determining topological protein combination patterns of a plurality of individual cells or cell membranes from said first cell sample;
    c) determining topological protein combination patterns of a plurality of individual cells or cell membranes from said second cell sample;
    d) subtracting the coincident parts of the topological protein combination patterns determined in b) and c) from the protein combination patterns determined in c), leaving a residual topological protein combination pattern comprising one or more proteins, wherein said one or more proteins of the residual topological protein combination pattern of step d) are identified as proteins specific to said modified cell type; and
    e) outputting said identified proteins.

16. A method for identifying disease-specific proteins, the method comprising the following steps:
    a) providing a first cell sample comprising cells of a first cell type, the cells affected by a disease, and a second cell sample comprising cells of a second type, the cells also affected by said disease;

b) determining topological protein combination patterns of a plurality of individual cells or cell membranes from said first cell sample;
c) determining topological protein combination patterns of a plurality of individual cells or cell membranes from said second cell sample;
d) subtracting the non-coincident parts of the topological protein combination patterns determined in b) and c) from either the protein combination patterns determined in b) or from the protein combination patterns determined in c), leaving a residual topological protein combination pattern comprising one or more proteins, wherein said one or more proteins of the residual topological protein combination pattern of step d) are identified as disease-specific proteins of said disease; and
e) outputting said identified proteins.

* * * * *